United States Patent [19]
Klaren

[11] Patent Number: 4,640,339
[45] Date of Patent: Feb. 3, 1987

[54] APPARATUS FOR CARRYING OUT PHYSICAL AND/OR CHEMICAL PROCESSES, MORE SPECIFICALLY A HEAT EXCHANGER OF THE CONTINUOUS TYPE

[75] Inventor: Dick G. Klaren, Hillegom, Netherlands

[73] Assignee: Esmil B.V., Amsterdam, Netherlands

[21] Appl. No.: 819,297

[22] Filed: Jan. 15, 1986

Related U.S. Application Data

[62] Division of Ser. No. 629,810, Jul. 11, 1984, Pat. No. 4,567,940.

[30] Foreign Application Priority Data

Jul. 22, 1983 [NL] Netherlands ............. 8302622

[51] Int. Cl.$^4$ ................. F28C 3/16; F28D 13/00
[52] U.S. Cl. ................. 165/1; 165/104.16; 34/57 A; 422/146
[58] Field of Search ........... 165/104.16; 34/57 A; 422/146

[56] References Cited

U.S. PATENT DOCUMENTS

| | | | |
|---|---|---|---|
| 2,488,406 | 11/1949 | Hirsch ................. | 422/146 |
| 3,476,655 | 11/1969 | Sieder ................. | 165/104.16 |
| 4,220,193 | 9/1980 | Klaren ................. | 165/104.16 |

FOREIGN PATENT DOCUMENTS

2087534  5/1982  United Kingdom ........... 165/104.16

Primary Examiner—Albert W. Davis, Jr.
Attorney, Agent, or Firm—Stevens, Davis, Miller & Mosher

[57] ABSTRACT

The invention relates to apparatus for carrying out physical and/or chemical processes, more specifically a heat exchanger (10) of the continuous type, comprising a large number of vertical heat exchanger tubes (18) mounted between a lower chamber (17) and an upper chamber (16) within a jacket (15). Within the tubes (18) small solid particles are kept in a fluidized condition by the fluid medium passing up from the lower chamber (17) through the tubes (18), so as to achieve a good heat transfer, whereas also any deposit will be removed from the inner tube walls. For the downward flow of the granular mass at least one return tube (21) is provided. Downward circulation of the fluid medium through the return tube (21) should be minimal. To stabilize the fluid bed in a riser tube the inflow pipe is provided with a lateral bore (23) and the top of the lower chamber above the level of the lateral bores (23) is fitted with an outlet 51 with a shutoff valve 52 to temporarily reduce pressure of the fluid medium at the top of the lower chamber should the lateral bores become clogged.

3 Claims, 12 Drawing Figures

APPARATUS FOR CARRYING OUT PHYSICAL AND/OR CHEMICAL PROCESSES, MORE SPECIFICALLY A HEAT EXCHANGER OF THE CONTINUOUS TYPE

This is a division of application Ser. No. 629,810, filed July 11, 1984, now U.S. Pat. No. 4,567,940, granted Feb. 4, 1986.

The invention relates to apparatus for carrying out physical and/or chemical processes, more specifically a heat exchanger of the continuous type, comprising a bundle of parallel vertical riser tubes, an upper chamber, a lower chamber, upper and lower tube plates for open connection of the tube bundle with the upper and lower chambers respectively, a granular mass that can be kept in a fluidised condition, at least in the riser tubes, by a fluid medium flowing during operation upwardly through the lower chamber, the riser tubes and the upper chamber, a distribution plate for the granular mass in the lower chamber, and at least one return tube opening below the distribution plate for return of an overflow of granular mass above the upper tube plate from the upper chamber to the lower chamber, wherein each riser tube is provided with an inflow element extending in the lower chamber, from the lower tube plate to a level above the distribution plate through which the return tube or return tubes projects or project, and wherein the lower chamber is provided with a device which prevents granules from reaching the lower chamber inlet for the fluid medium during standstill.

An apparatus of this type is known from an article by D. G. Klaren in "Fouling Prevention Research Digest", Vol. 5, No. 1 pp. III–XVII (March 1983). The known heat exchanger that because of the presence of the fluidised bed has a high efficiency as a result of breakage of the fluid film along the inner surface of the riser tubes is primarily of interest, if, from the fluid medium on the inner surface of the riser tubes, a layer of material can be deposited that impedes heat transfer through the riser tube walls. This impeding layer is not deposited in the known apparatus due to the abrasive action of the granules. Therefore the known apparatus is ideal for application in e.g. the food industry.

On the other hand the presence of the granular mass brings its disadvantages. One disadvantage of the known apparatus is that it is never completely certain that the downward flow of the granular mass will occur only in the return tube or the return tubes that are intended for the purpose. To achieve a correct design and to ensure an even distribution of both the fluid medium and the granular mass across all riser tubes it is of utmost importance that only tubes that are intended for the purpose serve as return tubes. The situation where one or more riser tubes will still start to function as return tubes can occur in particular if insufficient care is exercised at start-up of the heat exchanger. It is then possible that the fluidised granules inside several riser tubes reach the top ends thereof earlier than the granules in other riser tubes, which causes the granules issuing from the former riser tubes to flow through the upper chamber into the adjoining riser tubes that are not yet completely filled with fluidised granules. The result is disturbance of the pressure balance between the various tubes causing a downward flow of fluid medium and granules into one or several tubes that were not originally intended for such a downward flow.

The invention eliminates this first objection by means of a constriction at the ends of the riser tubes that open into the upper chamber.

In this constriction the velocity of the fluid medium is increased to such an extent that the granules cannot drop from the upper chamber back into a riser tube. With the constriction correctly dimensioned, even a high irregular distribution of the granular mass across the riser tubes with startup of the heat exchanger cannot cause one or several riser tubes to start acting as return tubes.

An advantageous construction of the apparatus is characterised by an upper pipe plate provided with apertures for the riser tibes having smaller cross-sections than the riser tubes themselves.

The granular mass circulates in the upward direction through the riser tubes and in the downward direction through the return tube. During this circulation, particularly in operation, granules are in eddying motion also in the lower chamber that apparently are the source of very severe wear of the heat exchanger jacket, especially of the material at the junction of the bottom cover and the cylindrical wall which forms part of the shell.

The second disadvantage is eliminated according to the invention by means of a second distribution plate arranged in the lower chamber at a level below the outlet therein of the return tube.

In this proposed construction, in contrast with the known apparatus, the device that impedes the granules from reaching, at standstill, the inlet for the fluid medium in the lower chamber cannot serve as a shutoff valve against the lower edge of the return tube. Consequently under all conditions a downward flow of the fluid medium will occur inside the return tube which, in the construction proposed, can amount to approx. 25 percent of the fluid medium mass flow supplied to the heat exchanger inlet. As the result the average logarithmic temperature difference inside the riser tubes will be less favourable which requires that, to achieve a desired efficiency, a larger heated surface must be installed.

The last requirement can be obviated to a certain degree according to the invention by constructing the distribution plate at a level above the return tube outlet into the lower chamber in multiple; preferably so that the apertures in the various distribution plates of the multiple construction are not vertically in line.

It appears that the downward flow of the fluid medium through the return tube or the return tubes can thus be limited to about 15 percent of the mass flow through the heat exchanger inlet.

The absence of any moving parts in the lower chamber, i.e. of the provision as a valve of the device that prevents granules from reaching, at standstill, the fluid medium inlet into the lower chamber, and the reduced wear of lower chamber parts offset the disadvantage of fluid medium circulation through the return tube.

To stabilise the fluidised bed in a riser tube it has been suggested to provide the inflow pipe element with a lateral bore at a level where, during operation, no granules are present in the lower chamber, i.e. where only the fluid medium is present. If strongly contaminating fluid media are used, e.g. fluid media that carry solids, the lateral bore may get clogged causing the fluidised bed in the riser tube to sag and finally causing the unintended functioning as a return tube of the riser tube, which must be defined as objectionable.

In a method of operation of apparatus of the type described at the outset, this last disadvantage is avoided by temporarily reducing the pressure of the fluid medium at the top of the lower chamber.

According to the invention, the apparatus of the type described at the outset is thereby characterised by lateral bores provided in the inflow pipe elements. The top of the lower chamber above the level of the lateral bores is fitted with an outlet with shutoff valve.

In particular the apparatus according to the invention is characterised in that the outlet at the top of the lower chamber is directly connected with a fluid medium outlet of the upper chamber.

The presence of a return tube or of return tubes has the associated disadvantage of causing displacement of the fluid medium from the upper chamber to the lower chamber. Although the granular mass flow inside the return tube will under some conditions stagnate and as it were clog up the return tube, in that case the intended average logarithmic temperature difference between the outer and inner surfaces of the riser tubes required for proper functioning of the heat exchanger will be adversely affected, unless by chance an operating point is found where this is not the case. However, such an operating point will entail undesirable restrictions and limitations of other operating parameters.

To be able at least to reduce this adverse effect the apparatus of the type described at the outset is characterised by a bypass between the inlet for the fluid medium used in the process in the lower chamber and a point in the upper chamber where the bypass opens into the upper chamber at the level of the inlet opening of the return tube or tubes.

Thus the bypass, which is preferably fitted with an adjustable valve to control the flow through it, will at least partly eliminate the temperature difference between the upper and the lower chambers.

According to the invention another solution of the same problem is provided in that a throttle device is located before the inlet opening of the return tube, which gives precedence to passage through the return tube to the fluid medium over that of the granular mass.

If the quantity of granular mass inside the return tube is thus limited less driving power will be available for circulation, which will cause reduced circulation through the return tube of granular mass and fluid medium.

Fouling can also occur on the outer wall of the riser tubes due to the nature of the second fluid medium used in the heat exchanging process. This particular problem relates to a more general class of heat exchangers, i.e. of the type where the second fluid medium that is used in the heat exchanging process is a fluid that, like a film, flows down the vertical riser tubes of apparatus for carrying out physical and/or chemical processes, more in particular a heat exchanger of the continuous type, consisting of a bundle of parallel vertical riser tubes, an upper chamber, a lower chamber, an upper pipe plate and a lower pipe plate for open connection of the pipe bundle with the upper and lower chambers, respectively, all for throughflow of the first fluid medium and an upper distribution chamber and a lower collecting chamber for throughflow of the second fluid medium, the upper distribution chamber closing around each riser tube leaving a gap in the bottom of the upper distribution chamber around each riser tube and the top of the lower collecting chamber being provided with collecting apertures around each riser tube.

Such apparatus is known from the article by D. G. Klaren in "Fouling Prevention Research Digest", Vol. 5, No. 1, pp. III–XVII (March 1983).

If the temperature and pressure occurring do not require that the fluid that is the second fluid medium is enclosed by a fixed jacket wall, the tubes can be easily cleaned from the outside, e.g. by washing down the pipe bundles which may be done during operation. However, if a very strongly fouling fluid is used as the second fluid medium in the heat exchanging process the bundles must be washed down so frequently that this is not practicable. Even if the process temperature and pressure do require that the second fluid medium is enclosed by a fixed jacket wall, this method for pipe bundle washing is out of the question. According to the invention optimal methods for cleaning the outer surfaces of the riser tubes are provided, in that all tubes have been fitted on the outside with a scraping device in a supporting construction that can be driven mechanically.

The scraping device of this type cannot reach the gaps in the bottom of the upper distribution chamber that may get clogged due to fouling.

To prevent the gaps from thus clogging up, or to at least delay the clogging process, the upper distribution chamber is provided, above its bottom, with a distribution shell that has apertures for distribution of the fluid over the gaps in the bottom.

Thus the gaps in the bottom can be wider without substantially increasing the height of the upper distribution chamber.

The invention in all its aspects will be illustrated below with a description referring to a plan. In the plan

Figure 1:
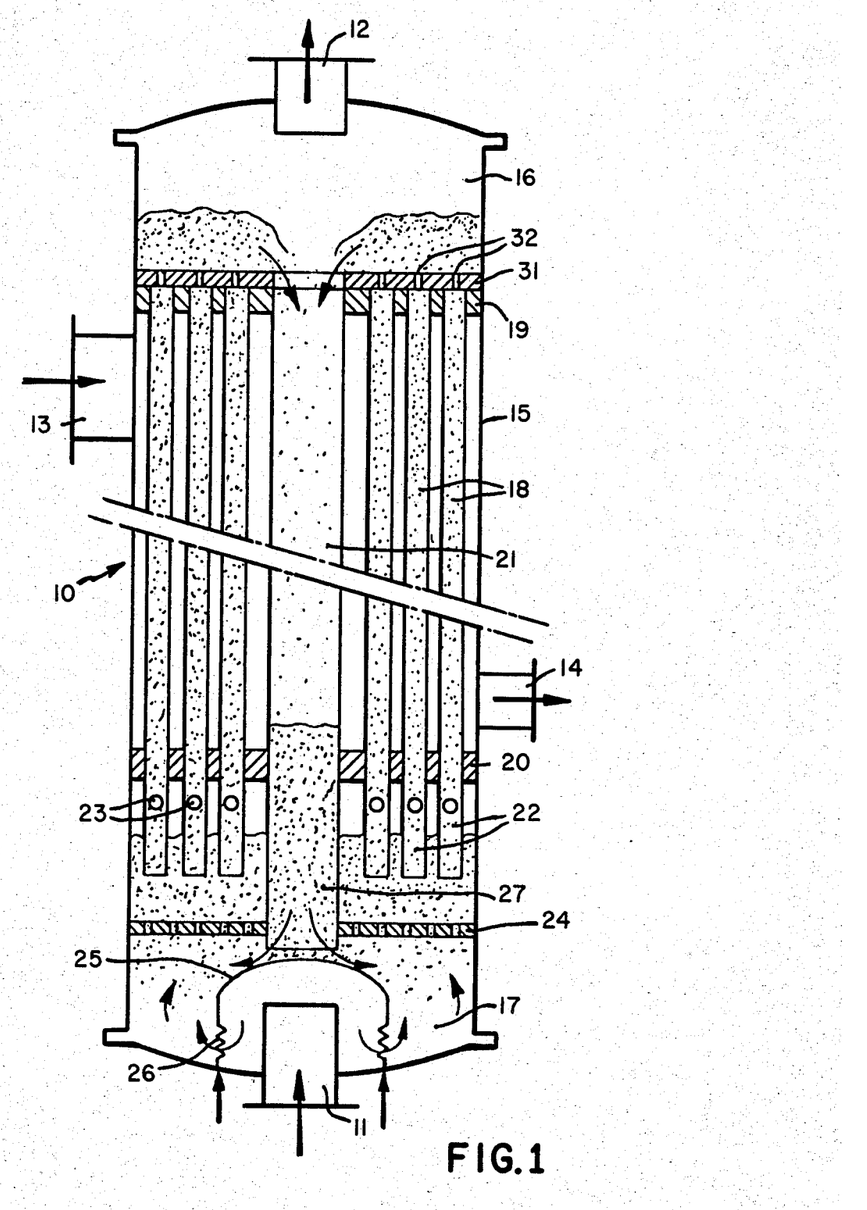
FIG. 1 shows an embodiment of a first aspect of the invention.

FIG. 1 shows an embodiment of the apparatus according to the first aspect of the invention. The heat exchanber 10 has, for a first fluid medium, an inlet 11 and an outlet 12 and, for a second fluid medium, an inlet 13 and an outlet 14. Inside the jacket 15 a lower chamber 17 connects to the inlet 11 and an upper chamber 16 connects to the outlet 12. A riser tube bundle 18 is arranged between an upper pipe plate 19 and a lower pipe plate 20, the riser tube bundle including a return tube 21. The riser tubes are provided with inflow pipe elements 22 that extend from the lower pipe plate 20 downwardly into the lower chamber 17. The inflow pipe elements are provided with lateral bores 23. In the lower chamber 17 a distribution plate 24 is located below the inlets of the riser tubes and above the outlet of the return tube. The lower chamber 17 is further provided with a device 25 that prevents the granules in the lower chamber, the riser tubes, the upper chamber and the return tube from reaching the inlet 11. The device 25 is mounted on a spring assembly 26 which, at standstill, presses the device 25 against the outlet aperture of the return tube. In any case the granules can be brought into the fluidised bed condition in the riser tubes 18. The lower end of the return tube 21 will contain a stagnating granular mass 27.

According to the invention the upper pipe plate 19 of the heat exchanger 10 is provided with throttling apertures 32 via which the riser tubes 18 open into the upper chamber 16. For instance the apertures 32 are provided in a throttle plate 31 constituting, within the assembly, an integral part of the upper pipe plate 19 and not forming an obstacle for the return tube 21.

It will be obvious that the throttling apertures 32 in the outlets of the riser tubes 18 are effective to prevent granules from dropping into the riser tubes from the upper pipe plate independently of the valve action of the device 25.

Figure 2:
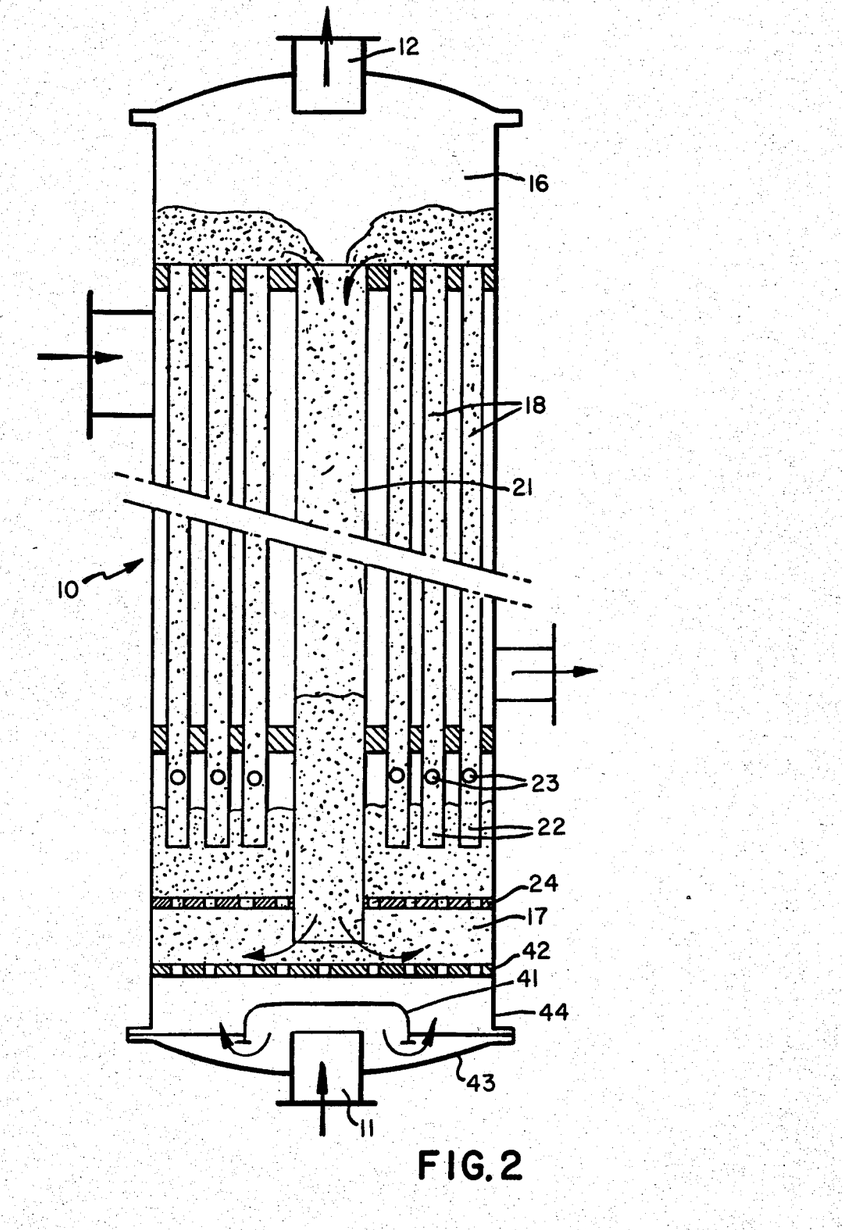
FIGS. 2 and 3 show embodiments of the invention according to a second aspect.
Figure 3:
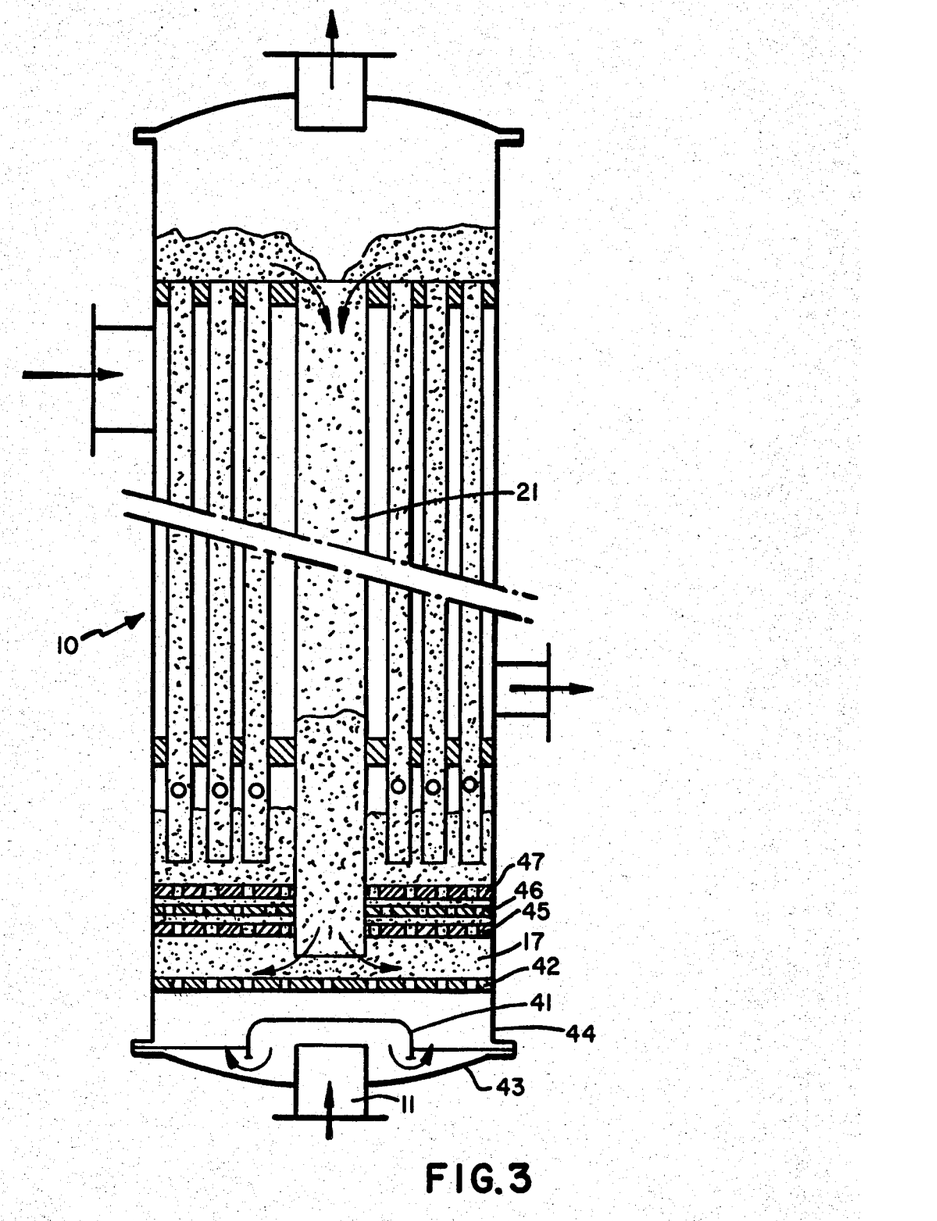

FIGS. 2 and 3 show embodiments of the invention according to a second aspect. The design of the apparatus in these embodiments corresponds in most respects with that shown in FIG. 1. To prevent the material of the jacket, particularly at the junction of the bottom cover 43 to the cylindrical wall 44, from being excessively worn due to the eddying motion of the granules constituting the material of the fluidised beds in the riser tubes, a second distribution plat 42 is provided in the lower chamber 17 at a level below the outlet in the lower chamber 17 of the return tube 21. The device that prevents granules from reaching, at standstill, the inlet 11 in the lower chamber 17 is provided as a simple bell 41 which is mounted fixedly and distributes the fluid medium from the projecting inlet 11 laterally through the lower chamber 17.

At standstill of the heat exchanger the majority of the granular mass will be present in the lower chamber, below the first distribution plate 24. At start-up the fluid medium flow from the inlet 11 will try to follow the least obstructed route. Initially the fluid medium will flow mainly through the return tube 21, but as the granular mass is carried in fluidised state by the fluid medium flow the medium passing through the return tube will gradually meet with greater resistance, causing the fluid medium to start rising also in the riser tubes 18 with simultaneous fluidisation of the granular mass inside the riser tubes. A further increase of the fluid medium mass flow will cause the fluidised beds inside the riser tubes 18 to rise faster than the fluidised bed inside the return tube 21. This is due to the lateral bores 23 in the inflow pipe lengths 22 that cause the fluidised bed inside the riser tubes to have a higher porosity than the bed inside the return tube. The fluidised granular mass in the riser tubes will first reach the upper chamber 16 and overflow into the return tube 21 through which the granular mass and the fluid medium will start to flow down. In the lower chamber 17 between distribution plates 24 and 42 the downward flow through the return tube 21 and the upward fluid medium flow from the inlet 11 will be mixed, and finally a balanced state occurs where the volume of fluid medium leaving the heat exchanger via outlet 12 equals the volume that enters the heat exchanger through inlet 11 and the granular mass is circulating through the riser tubes 18 and the return tube 21. During the circulation process the riser tubes 18 are less heavily charged with granular mass than the return tube 21. To suppress the adverse effect on the average logarithmic temperature difference due to the fluid medium flow through the return tube, circulation of the fluid medium through the return tube should be minimal. An increase of the pressure difference between the upper and lower chambers contributes to reducing the fluid medium flow through the return tube. The increase of the pressure difference is achieved by fitting several distribution plates at a level above the return tube outlet into the lower chamber, preferably so that the apertures in the various distribution plates of the multiple design are not vertically in line. FIG. 3 shows the multiple distribution plate design 45,46,47 in the lower chamber 17 above the return tube 21 outlet.

Figure 4:
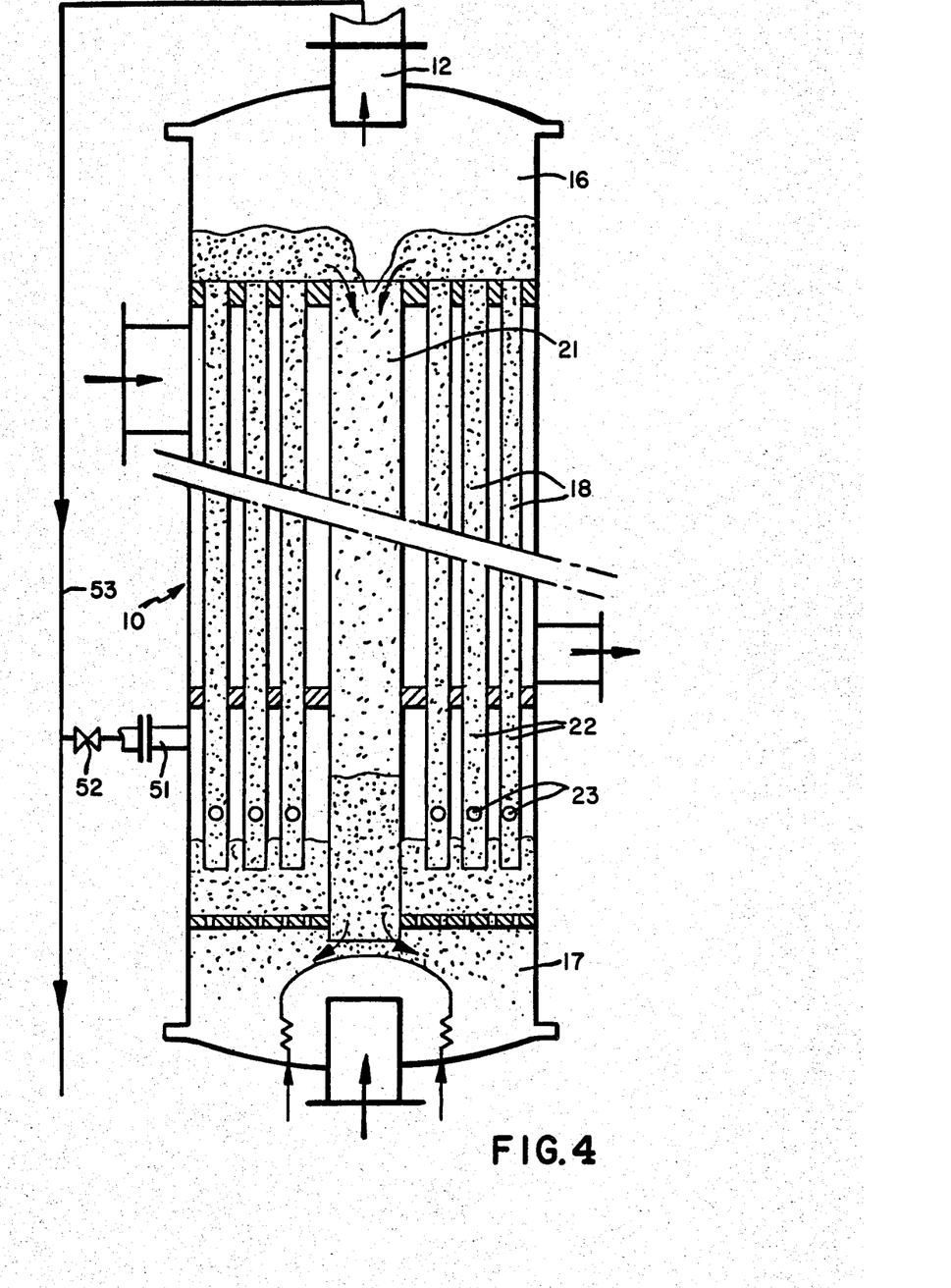
FIGS. 4 and 5 show embodiments of the invention according to a third aspect.
Figure 5:
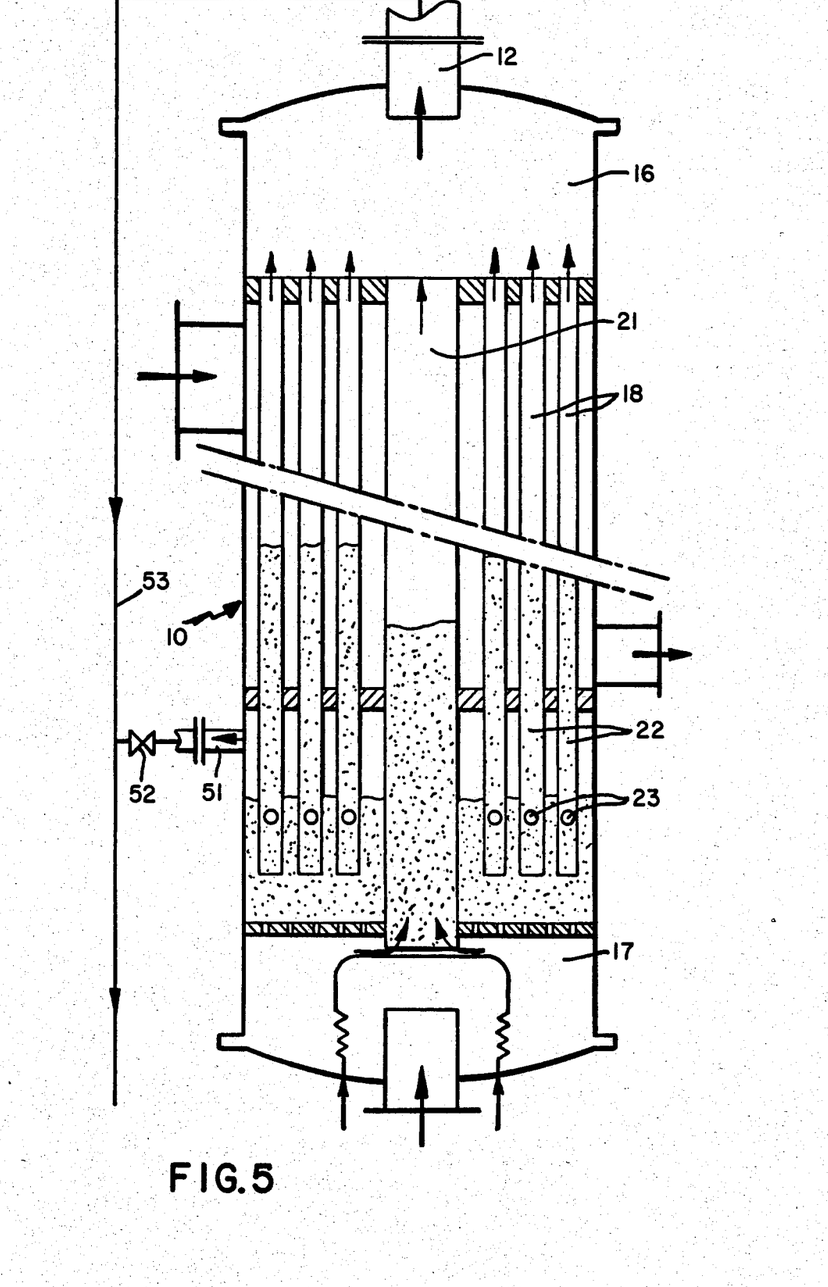

FIGS. 4 and 5 illustrate the operation and design of the device for cleaning the lateral bores in the inflow pipe elements of the riser tubes. FIG. 4 shows the heat exchanger 10 as it is shown in FIG. 1 under normal operating conditions, the riser tubes 18 functioning normally. From FIG. 4 is appears that the upper section of the lower chamber 17 is connected, by a pipe 51 provided with a shutoff valve 52, to a discharge line 53 that carries off the flowing fluid medium from the outlet 12. During normal operation the shutoff valve 52 is closed. The lower chamber 17 contains a granular mass volume in fluidised condition up to a level just below the lateral bores 23 in the inflow pipe lengths 22. Fluidised granular mass is further present in the riser tubes 18 and in the upper chamber 16. In the riser tubes 18 the granular mass and the fluid medium move upward and downward in the return tube 21. If a lateral bore in an inflow pipe length of a riser tube clogs up the upward flow inside that riser tube may suddenly change into a downward flow. To avoid this undesirable situation it should be possible to remove any dirt deposits on the outer surface of the inflow pipe element. This is achieved by partly opening the shutoff valve 52. This will cause part of the fluid medium to flow to the discharge line 53 via the lower chamber 17 and the partly opened shutoff valve 52. The fluidised granular mass in the riser tubes 18 will sag to a level e.g. half the height of the riser tubes, and the upper chamber 16 will not contain any more granular mass at all. Under such conditions the return tube 21 will function as a partly filled riser tube. In the lower chamber 17 the volume of fluidised granular mass will be growing substantially, which will cause the granular mass to extend beyond the lateral bores 23 while yet keeping an adequate distance between the mass and the connection of pipe 51 to the lower chamber in order to prevent any granular mass from being carried off with the fluid medium. The abrasive action of the fluidised granular mass on the lateral bores in the inflow pipe lengths will remove the fouling deposits and carry them off via the pipe 51.

FIG. 5 shows the position of the fluidised granular mass inside the system, with the shutoff valve 52 in the partly open position. It appears that the operating condition, which varies in that the shutoff valve 52 is partly open so that the lateral bores are being cleaned, has to be maintained for only a few dozen seconds, which is not generally considered objectionable. For inspection of the level of the fluidised granular mass in the lower chamber 17 during cleaning of the lateral bores in the inflow pipe elements, simple pressure difference measurement will be sufficient. When the shutoff valve 52 closes again the system will return to the original operating condition.

As already said, a disadvantage of an apparatus of the type described at the outset is that sometimes the circulation within the system of the fluid medium and of the granular mass produces an excessively adverse effect on the average logarithmic temperature difference across the heat exchanger. The main source of the problem is fluid medium circulation.

Figure 6:
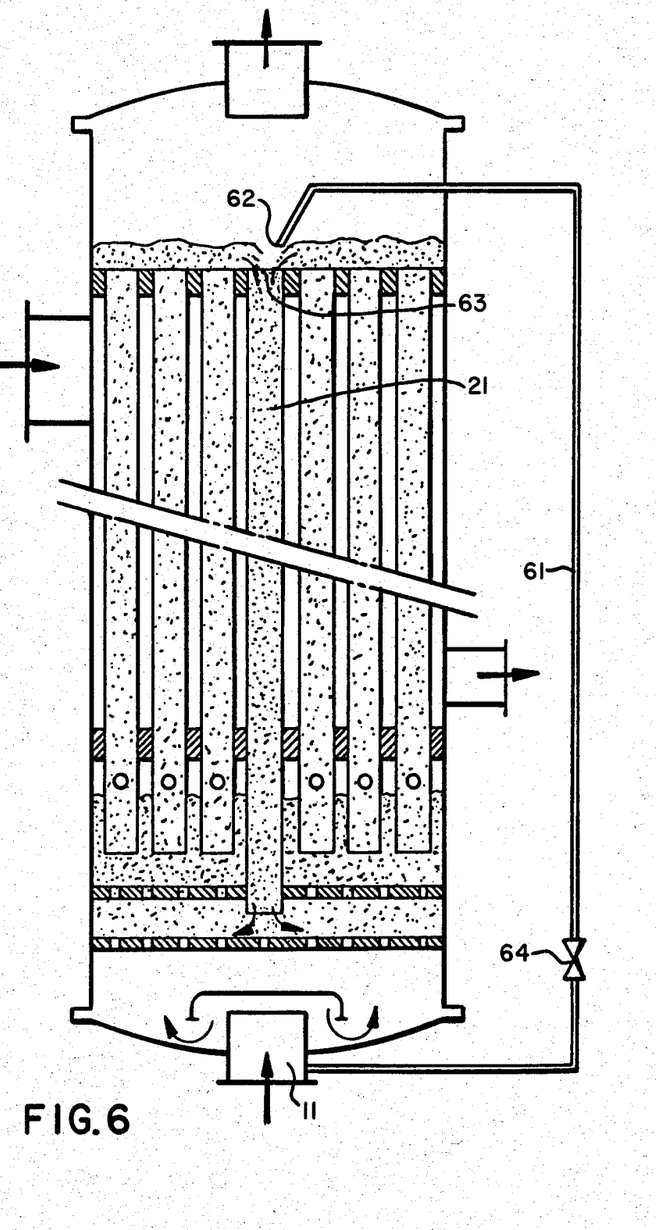
FIG. 6 shows an embodiment of the invention according to a fourth aspect.

FIG. 6 shows an embodiment of a suitable solution for this problem that consists of providing a bypass 61 between the inlet 11 which opens into the lower chamber 17 for the fluid medium taking part in the process and a position 62 in the upper chamber 16 at which the bypass 61 opens at the level of the inlet 63 of the return tube 21.

The bypass is provided with an adjustable valve 64. At start-up of the heat exchanger it is recommended to keep the shutoff valve 64 in the bypass 61 closed. When the system is in a stable operating condition the shutoff valve 64 can be gradually opened to partly or fully open depending on the process requirements. A fluid medium flow with a temperature equal to the entry temperature of the fluid medium in the lower chamber 17 is now present in the immediate area of the inlet opening 63 of the return tube. As the result the average temperature inside the return tube will be nearer to the entry temperature of the fluid medium in the lower chamber than it would be in the absence of the bypass, which produces the beneficial effect referred to earlier. The bypass can also be located inside the heat exchanger.

Figure 7:
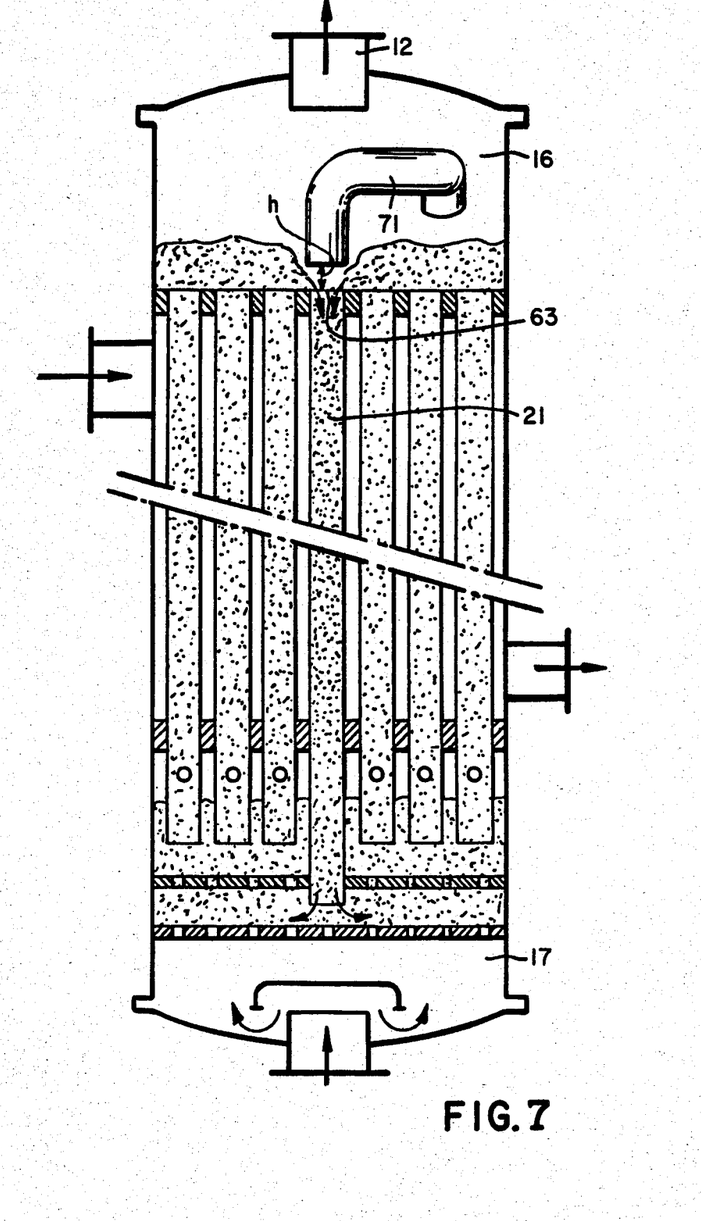
FIGS. 7 and 8 show an embodiment of the invention according to a fifth aspect.
Figure 8:
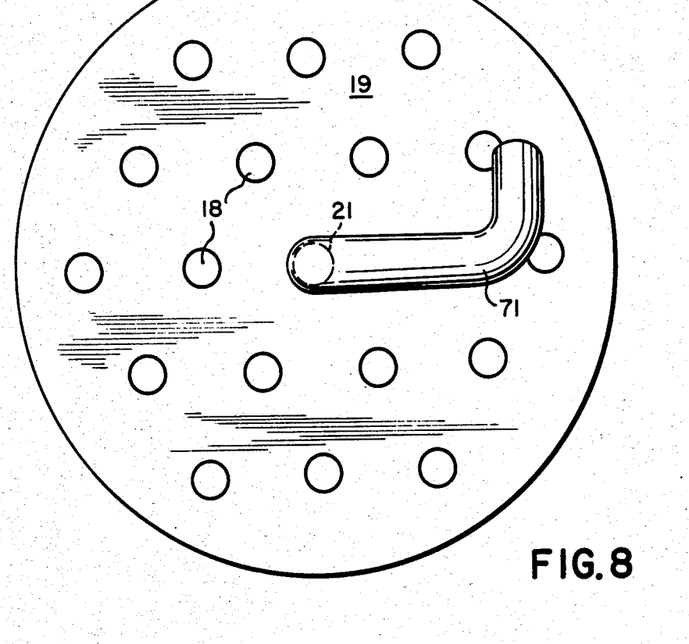

Another solution for the problem that is solved by the embodiment of FIG. 6 is according to the invention achieved by locating a throttle device in front of the return tube inlet that gives precedence to passage of the fluid medium through the return tube over passage of the granular mass. FIGS. 7 and 8 show an embodiment of this other solution. In FIG. 7 the throttle device 71 is a pipe that is provided as a continuation of the return tube 21 at a distance h from the inlet 63 of the return tube in the upper chamber 16. In principle, the throttle device 71 can consist of a straight pipe length the top end of which extends far enough into the upper chamber 16 to prevent granules from dropping through the straight pipe into the return tube 21 during all normal operating conditions. Experimental results have shown that the distance h affects the rate of circulation of the granular mass and the fluid medium flow through the return tube. For correct adjustment of the circulation rate the distance h must satisfy the condition:

$$0.1 \times Dv < h < 2.0 \times Dv$$

where Dv is the inner diamter of the return tube above which the throttle device is positioned.

By slightly changing the shape of the throttle device, the device will be capable of performing yet another function. If insufficient care is exercised at start-up of the heat exchanger, the return tube may, as mentioned earlier, start to operate as a reiser tube carrying very large volumes of fluid medium and granular mass from the lower chamber 17 to the upper chamber 16. As the result the throttle device of the straight pipe type can blow the granules very high into the upper chamber and granules may be lost via outlet 12 for the fluid medium. This is an undesirable situation. By selecting a suitable inner diameter of the throttle device of the straight pipe type, and by bending the pipe at the top from the vertical plane into the horizontal plane and then bending it slightly down and again over an angle of about 90 degrees the granules and the fluid medium that are brought at high velocity out of the return tube 21 are trapped in the bent pipe and are further guided so that the granules remain in the upper chamber. FIG. 8 shows a top view of the design as a cross-section of the upper chamber illustrating how the pipe to be used as a throttle device must be bent. The inner diameter of the throttle device of the bent pipe type must exceed the inner diameter of the return tube to prevent granules from being lost.

A next aspect of the invention relates to apparatus for carrying out physical and/or chemical processes, in particular a heat exchanger of the continuous type, consisting of a bundle of parallel vertical riser tubes, an upper chamber, a lower chamber, an upper pipe plate and a lower pipe plate for open connection of the pipe bundle to the upper and lower chambers respectively, all of which are provided for throughflow of a first fluid medium, and an upper distribution chamber and a lower collecting chamber for throughflow of a second fluid medium, the bottom of the upper distribution chamber closing around each riser tube leaving a gap between the bottom of the upper distribution chamber and the riser tube wall, the top of the lower collecting chamber being open.

Figure 9:
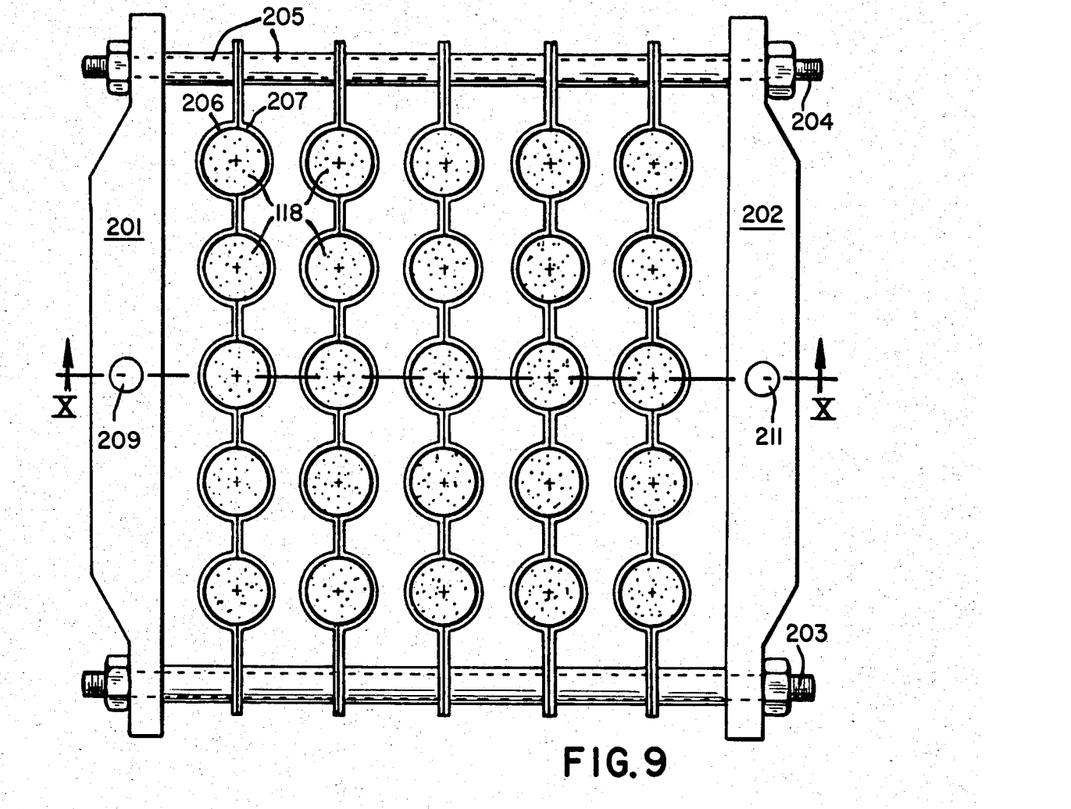
FIGS. 9 and 10 show an embodiment of the invention according to a sixth aspect.
Figure 10:
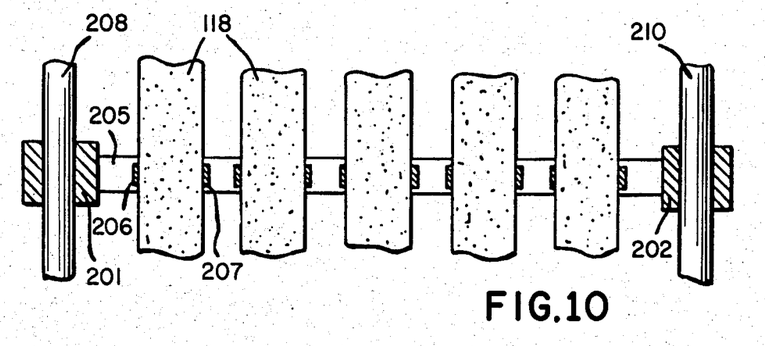

In this apparatus, the second fluid medium is a fluid that flows down as a film along the vertical riser tubes in counterflow with the first fluid medium that rises inside the riser tubes. For optimal cleaning of the outer surface of the riser tubes or the outer surface of other pipes of the same bundle all tubes and pipes are fitted on the outside with a scraping device mounted in a supporting assembly that can be driven mechanically. FIG. 9 shows an embodiment of the scraping device, i.e. a top view perpendicular to the pipes. In a frame consisting mainly of two yokes 201,202 and two crossbars 203,204, spacers 205 are used to mount strips 206,207 that fit closely around the riser tubes 118. The frame is displaced in the longitudinal direction along the riser tubes by means of a spindle 208 that engages in a threaded hole 209 in the yoke 201. The yoke 202 is guided by a rod 210 that passes through a hole 211 in the yoke. This is illustrated in FIG. 10 which shows a cross section of the scraping device in FIG. 9 along the line X—X shown in that figure. To allow mounting of the scraping device in the heat exchanger the strip width must not exceed the free gap between the pipe rows in the bundle.

Figure 11:
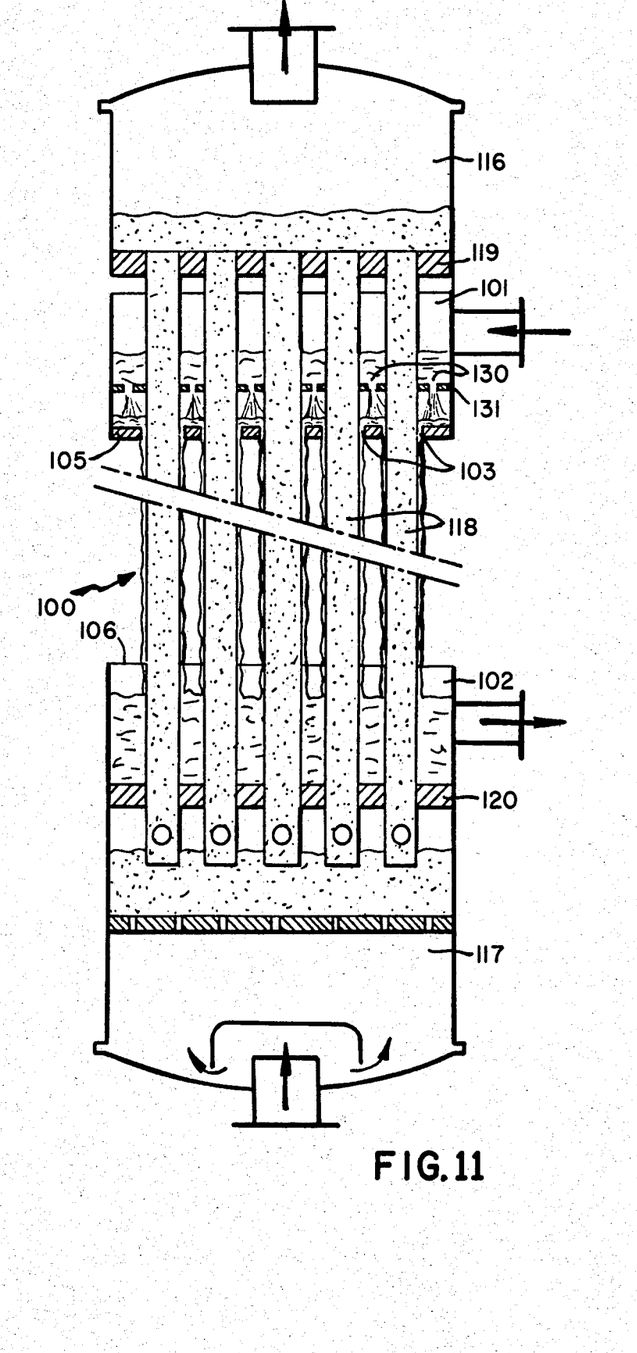
FIGS. 11 and 12 show an embodiment of the invention according to a seventh aspect.

In a system of the last-described type, particularly the gaps in the bottom of the upper distribution chamber that allow the fluid to flow from the upper distribution chamber to the film around the riser tubes can get clogged. To reduce the risk of these gaps clogging up, in accordance with the invention at least one distribution shell is arranged in the upper distribution chamber above the base; the shell is provided with apertures for distribution of the fluid over the gaps in the base. FIG. 11 shows apparatus 100 of the type described, having an upper chamber 116, a lower chamber 117 and a pipe bundle 118 for throughflow of the first fluid medium, and an upper distribution chamber 101 and a lower collecting chamber 102 for throughflow of a second fluid medium, wherein the upper distribution chamber 101 closes around each riser tube 118 so as to leave a gap 103 in the bottom 105 of the upper distribution chamber of the riser tube and wherein the top 106 of the lower collecting chamber 102 is open.

Figure 12:
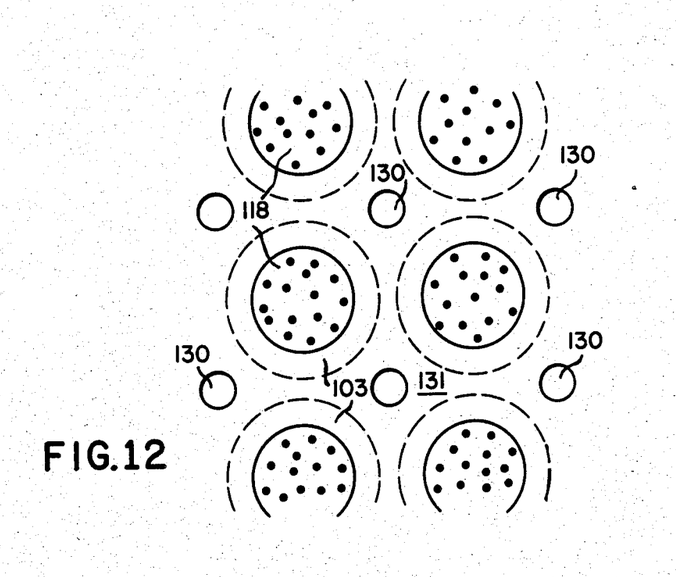

The upper distribution chamber is provided with a distribution plate 131 with apertures 130 centred between the riser tubes 118 which extend through the upper distribution chamber. The presence of the distribution plate 131 allows gaps 103 of greater width than is otherwise possible. FIG. 12 which shows a top view of a section of the distribution plate 131, illustrates the centred positions of the apertures 130 between the riser tubes 118. For the sake of clarity, the scale ratios do not correspond with an actual embodiment.

As to the operation of the system, the fluid flowing down through the apertures 130 splashes outwardly on the bottom 105 and so reaches the outer walls of the riser tubes and runs down them as a film. Thus the gap 103 does not need to contribute essentially to the formation of the film. To ensure that the fluid jet will splash outwardly through an aperture 130 a suitable distance must be maintained between the distribution plate 131 and the bottom 105.

It is remarked that, whereas the distribution plate referred to above has been provided with apertures, these apertures may also be fitted with tuyeres, or spray nozzles, that cause lateral outflow from an aperture.

To ensure stable operation of the various systems described above, the pressure drop in the fluid medium flow over the distribution plate into the lower chamber directly below the riser tubes must be in excess of one-tenth of the pressure drop due to the total weight of the granular mass, as defined in the article quoted earlier and is illustrated in Dutch patent application No. 7703939.

What is claimed is:

1. Method of operation of apparatus for carrying out physical and/or chemical processes, in particular a heat exchanger of the continuous type, comprising a bundle of parallel vertical riser tubes, an upper chamber, a lower chamber, an upper pipe plate and a lower pipe plate for open connection of the pipe bundle to the upper and lower chambers respectively, a granular mass that can be kept in a fluidised condition at least in the riser tubes by a fluid medium flowing during operation upwardly through the lower chamber, the riser tubes and the upper chamber, a distribution plate for the granular mass in the lower chamber and at least one return tube with outlet below the distribution plate for return of an overflow of granules above the upper pipe plate from the upper chamber to the lower chamber, wherein each riser tube is provided with an inflow pipe element extending into the lower chamber from the lower pipe plate to a level above the distribution plate through which the return tube or tubes projects or project, and the lower chamber is provided with a device that prevents granules from reaching the lower chamber inlet for the fluid medium at standstill characterised in that the fluid medium pressure at the top of the lower chamber is temporarily reduced.

2. Apparatus for carrying out physical and/or chemical processes, in particular a heat exchanger of the continuous type, comprising a bundle of parallel vertical riser tubes, an upper chamber, a lower chamber, an upper pipe plate and a lower pipe plate for open connection of the pipe bundle with the upper and lower chambers respectively, a granular mass that can be kept in a fluidised condition at least in the riser tubes by a fluid medium flowing during operation upwardly through the lower chamber, the riser tubes and the upper chamber, a distribution plate for the granular mass in the lower chamber, and at least one return tube with outlet below the distribution plate for return of an overflow of granules above the upper pipe plate from the upper chamber to the lower chamber, wherein each riser tube is provided with an inflow pipe element extending into the lower chamber from the lower pipe plate to a level above the distribution plate through which the return tube or tubes projects or project, and the lower chamber is provided with a device that prevents granules from reaching the lower chamber inlet for the fluid medium at standstill, characterised in that in the case in which the inflow pipe elements (22) are provided with lateral bores (23), the top of the lower chamber (17) is provided at a level above the lateral bores (23) level, with an outlet (51) with shutoff valve (52).

3. Apparatus according to claim 2, characterised in that the outlet (51) at the top of the lower chamber (17) is directly connected to an outlet (53) of the upper chamber (16) for the fluid medium.

* * * * *